(12) United States Patent
Murray et al.

(10) Patent No.: US 9,393,010 B2
(45) Date of Patent: Jul. 19, 2016

(54) SUTURING INSTRUMENT FOR PASSING MULTIPLE SUTURES

(71) Applicant: Arthrex, Inc., Naples, FL (US)

(72) Inventors: R. Pepper Murray, Bountiful, UT (US); Jonathan I. Decker, Wellsville, UT (US); Robert M. Weber, Chino Hills, CA (US); Thomas Dooney, Jr., Naples, FL (US); Jacob L. Powell, North Ogden, UT (US)

(73) Assignee: Arthrex, Inc., Naples, FL (US)

( * ) Notice: Subject to any disclaimer, the term of this patent is extended or adjusted under 35 U.S.C. 154(b) by 87 days.

(21) Appl. No.: 13/912,829

(22) Filed: Jun. 7, 2013

(65) Prior Publication Data
US 2013/0345725 A1 Dec. 26, 2013

Related U.S. Application Data

(63) Continuation of application No. 12/614,285, filed on Nov. 6, 2009, now Pat. No. 8,460,318.

(60) Provisional application No. 61/112,533, filed on Nov. 7, 2008.

(51) Int. Cl.
| *A61B 17/04* | (2006.01) |
| *A61B 17/062* | (2006.01) |
| *A61B 17/06* | (2006.01) |

(Continued)

(52) U.S. Cl.
CPC ........... *A61B 17/0469* (2013.01); *A61B 17/062* (2013.01); *A61B 17/0625* (2013.01); *A61B 17/0482* (2013.01); *A61B 17/0483* (2013.01); *A61B 2017/06019* (2013.01); *A61B 2017/06042* (2013.01); *A61B 2017/2837* (2013.01); *A61B 2017/2912* (2013.01); *A61B 2017/2925* (2013.01); *A61B 2017/2926* (2013.01)

(58) Field of Classification Search
CPC ............. A61B 17/0469; A61B 17/062; A61B 17/0625; A61B 17/0491; A61B 17/0482; A61B 17/0483; A61B 2017/047; A61B 2017/00663; A61B 2017/0488; A61B 17/128; A61B 17/1285; A61B 2017/0409; A61B 2017/0416; A61B 2017/06042; A61B 17/04; A61B 17/0401
See application file for complete search history.

(56) References Cited

U.S. PATENT DOCUMENTS

| 3,901,244 A | * | 8/1975 | Schweizer | ............. A61B 17/04 206/63.3 |
| 5,431,666 A | | 7/1995 | Sauer et al. | |
| 5,522,820 A | * | 6/1996 | Caspari et al. | ................. 606/148 |

(Continued)

FOREIGN PATENT DOCUMENTS

| EP | 1 958 574 A1 | 8/2008 |
| WO | WO 2007/019016 A1 | 2/2007 |

*Primary Examiner* — Christopher L Templeton
(74) *Attorney, Agent, or Firm* — Blank Rome LLP (57) ABSTRACT

An instrument for passing sutures in tissue repair and/or other mini-open procedures. The instrument includes a pair of jaws mounted on a distal end of a shaft, a hand assembly mounted on a proximal end of the shaft, and a needle mounted on the hand assembly and through a cannulation of the shaft. The pair of jaws includes a lower jaw and an upper jaw, the lower jaw being provided with a slot configured to engage a plurality of sutures. The hand assembly has a finger lever with a ratchet and a releaser with a hook, the hand assembly being designed to move the needle from a first position to a second position, and to sequentially engage the needle with each of the plurality of sutures.

10 Claims, 13 Drawing Sheets

(51) Int. Cl.
*A61B 17/28* (2006.01)
*A61B 17/29* (2006.01)

(56) References Cited

U.S. PATENT DOCUMENTS

| | | | |
|---|---|---|---|
| 5,797,927 A * | 8/1998 | Yoon | 606/144 |
| 6,245,079 B1 | 6/2001 | Nobles et al. | |
| 6,770,084 B1 | 8/2004 | Bain et al. | |
| 6,896,686 B2 | 5/2005 | Weber | |
| 7,585,305 B2 | 9/2009 | Dreyfuss | |
| 7,722,630 B1 * | 5/2010 | Stone | A61B 17/0491 606/144 |
| 7,879,046 B2 * | 2/2011 | Weinert et al. | 606/139 |
| 7,879,048 B2 | 2/2011 | Bain et al. | |
| 7,883,517 B2 | 2/2011 | Pantages et al. | |
| 7,972,344 B2 | 7/2011 | Murray et al. | |
| 8,267,947 B2 | 9/2012 | Pantages et al. | |
| 2003/0065337 A1 | 4/2003 | Topper et al. | |
| 2003/0233106 A1 | 12/2003 | Dreyfuss | |
| 2004/0015177 A1 * | 1/2004 | Chu | A61B 17/0469 606/139 |
| 2004/0034372 A1 * | 2/2004 | Chu | 606/148 |
| 2005/0288690 A1 | 12/2005 | Bourque et al. | |
| 2006/0069407 A1 | 3/2006 | Weber | |
| 2006/0293699 A1 * | 12/2006 | Robertson | A61B 17/0482 606/144 |
| 2007/0032799 A1 | 2/2007 | Pantages et al. | |
| 2007/0032801 A1 | 2/2007 | Pantages et al. | |
| 2007/0118150 A1 * | 5/2007 | Weber | 606/139 |
| 2007/0225735 A1 * | 9/2007 | Stone et al. | 606/144 |
| 2007/0255317 A1 * | 11/2007 | Fanton | A61B 17/062 606/232 |
| 2007/0270885 A1 * | 11/2007 | Weinert | A61B 17/0469 606/139 |
| 2008/0097482 A1 | 4/2008 | Bain et al. | |
| 2008/0208221 A1 | 8/2008 | Murray et al. | |
| 2009/0005793 A1 | 1/2009 | Pantages et al. | |
| 2009/0062816 A1 | 3/2009 | Weber | |
| 2009/0062819 A1 | 3/2009 | Burkhart et al. | |
| 2009/0088781 A1 * | 4/2009 | Prestel | A61B 17/0469 606/148 |
| 2009/0131956 A1 | 5/2009 | Dewey et al. | |
| 2010/0121352 A1 | 5/2010 | Murray et al. | |

* cited by examiner

SUTURING INSTRUMENT FOR PASSING MULTIPLE SUTURES

CROSS-REFERENCE TO RELATED APPLICATIONS

This is a continuation of U.S. application Ser. No. 12/614,285, filed Nov. 6, 2009, now U.S. Pat. No. 8,460,318, which claims the benefit of U.S. Provisional Application No. 61/112,533, filed Nov. 7, 2008, the entire disclosures of which are incorporated by reference herein.

FIELD OF THE INVENTION

The present invention relates to the field of surgery and, more particularly, to a suture passing instrument configured to pass multiple sutures independently through tissue.

BACKGROUND OF THE INVENTION

Both open and endoscopic surgical procedures often require sutures to ligate, join or otherwise treat tissue. Generally, suture needles with attached suture strands are grasped either manually or by forceps and passed through the desired work site so a knot can be tied. While the procedures are fairly uncomplicated in open surgery where most suture sites are readily accessible, in endoscopic procedures, where access to the work site is not readily available, the surgeon must use auxiliary devices to be able to grasp the suture strands and pass them through desired tissue.

Although various instruments and techniques have been developed for surgical repairs requiring the passing of sutures to distant locations, instruments that allow a surgeon to quickly, accurately, and easily pass multiple sutures through soft tissue are still needed.

SUMMARY OF THE INVENTION

The present invention provides a suture passing instrument and surgical technique for surgical repairs. The suture passing instrument comprises an elongated tubular member and a tip configured to be loaded with a plurality of flexible strands (such as sutures, for example) that are passed independently and without the need to pull the instrument out of the surgical site to reload the sutures.

Other features and advantages of the present invention will become apparent from the following description of the invention which refers to the accompanying drawings.

DETAILED DESCRIPTION OF THE INVENTION

The present invention provides a suture passing instrument and technique for surgical repairs. The suture passing instrument comprises an elongated tubular member and a tip configured to be loaded with a plurality of flexible strands (such as sutures) that are passed independently and without the need to pull the instrument out of the surgical site to reload the sutures. The sutures are loaded onto the instrument outside of the surgical site, and then are independently passed inside the surgical site (without the need to pull the instrument out of the surgical site to reload the sutures). A bendable needle passes the sutures from the instrument through the tissue at the surgical site.

The suture passing instrument generally comprises an elongated tubular member with a handle assembly located at the proximal end and a tip located at the distal end. The tip comprises a fixed lower jaw and an upper movable jaw. The handle assembly provides for opening and closing of the upper jaw coupled to the tip of the instrument. A ratcheting mechanism provides for locking and unlocking of the jaw as desired by the user. Additionally, the handle assembly houses a mechanism for advancing and retracting the needle.

A first suture is loaded into a slot of the lower jaw of the instrument. By actuating a spring loaded thumb pad, a needle is pushed forward to allow the first suture to shift into the slot of the needle. Upon release of the thumb pad, the needle is retracted to the original position, and a second suture is loaded onto the slot of the lower jaw of the instrument. The handle assembly of the instrument is squeezed to advance the needle, so that the first suture is now distal the second suture. The instrument: is now loaded. The jaws are opened to grasp tissue and closed to hold tissue using the finger lever and ratcheting mechanism. Once the instrument is in position, the first suture is passed through tissue by squeezing the handle assembly together. The needle is then retracted (for example, fully retracted) by releasing pressure on the handles; the jaws are opened to move the instrument to an adjacent region of the tissue and closed again. Squeezing the first and second handles again captures and advances the second suture through an adjacent region of tissue.

Referring now to the drawings, where like elements are designated by like reference numerals, FIGS. 1-15 illustrate various structural elements of suture passing instrument 100 of the present invention provided with a jaw configured to allow at least two flexible strands to be loaded thereon and a handle assembly allowing the two strands to be passed independently (and without the need to remove the instrument from the surgical site to reload it with an additional strand).

As shown in FIGS. 5-13, suture passing instrument 100 comprises an elongated tubular member or shaft 12 having a longitudinal axis, a proximal end 11, a distal end 13 and an axial throughbore therein (not shown). Shaft 12 may be a tube or a narrow-diameter rod of dimensions that permit the tubular member to be introduced through an associated cannula (for example, an 8.25 cannula) in a minimally invasive procedure, such as arthroscopic or other endoscopic procedures, or into a body cavity, such as the abdominal cavity. Alternatively, shaft 12 may be an open U channel (and not a closed tube).

Elongated tubular member 12 extends between a handle assembly 20 and a tip 10 consisting of a pair of jaws comprising an upper jaw 10a and a lower jaw 10b. Lower jaw 10b is provided at the distal end 13 of the instrument and is preferably integral with the tubular member 12. Upper jaw 10a forms part of the tip 10 and may pivot with respect to the tip or lower jaw 10b. As illustrated in FIGS. 5-13, lower jaw 10b is substantially straight with respect to the shaft, while the upper jaw 10a is either straight or curved, and may be provided with a plurality of teeth to enhance tissue grasping and suture passing stability. In an exemplary embodiment, the upper jaw 10a is curve-shaped, preferably hump-back shaped, having a certain radius of curvature and is pivotally connected to the lower jaw 10b. The upper jaw 10a is designed to accommodate tissue to be grasped between the upper and the lower jaws, 10a, 10b.

The bottom jaw 10b of the instrument is illustrated in more detail in FIGS. 1-4. The bottom jaw 10b includes a longitudinal channel 16 and a securing mechanism 17 provided at the distal end of the lower jaw 10b. In exemplary embodiments, the securing mechanism 17 may be a suture loading slot 17 in communication with the longitudinal channel 16. The longitudinal channel and the securing mechanism (loading slot) are configured to allow at least one suture (or at least a strand of flexible material) to extend therethrough and to be securely positioned within the securing mechanism (loading slot). Slot 17 may have various configurations, for example, a groove (such as a V groove) or a wedge, to allow multiple suture positioning for future suture manipulation with the construct of the invention. The securing mechanism 17 is formed integrally with the lower jaw 10b.

Figure 1:
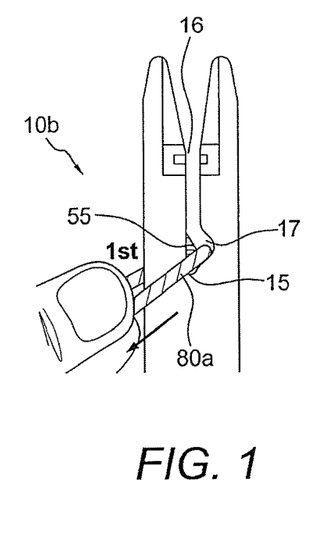
FIG. 1 illustrates a top view of a lower jaw of a suture passing instrument of the present invention, with a first flexible strand positioned thereon and adjacent a needle.
Figure 2:
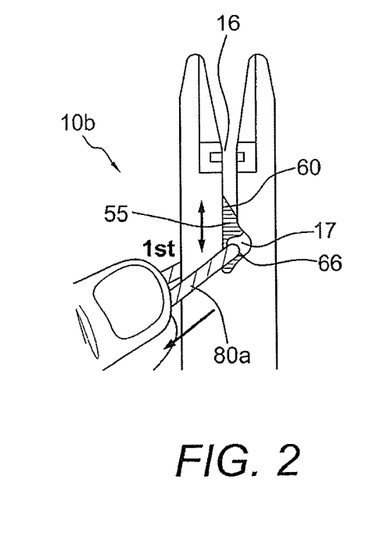
FIG. 2 illustrates a top view of the lower jaw of the suture passing instrument of FIG. 1, with the needle advanced and the first flexible strand shifted into the slot of the needle.
Figure 2A:
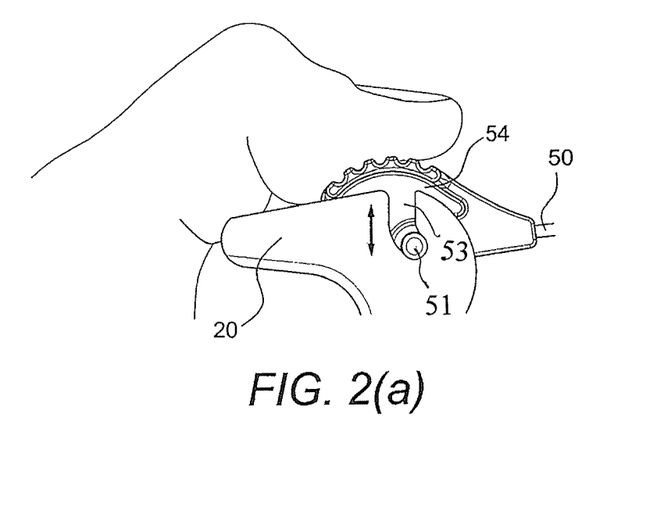
FIG. 2(a) illustrates a view of a proximal end of the suture passing instrument of FIG. 1, with the thumb pad down to advance the needle until the first flexible strand shifts into the slot of the needle.
Figure 3:
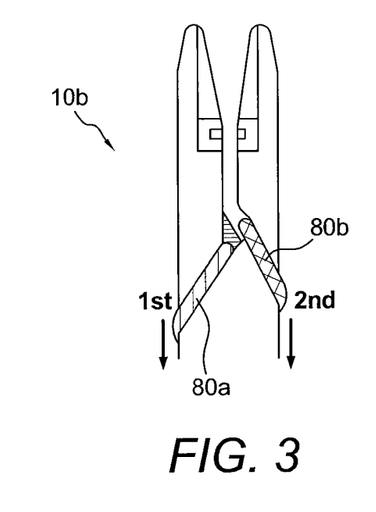
FIG. 3 illustrates a top view of the lower jaw of the suture passing instrument of FIG. 1, with a second flexible strand positioned thereon.

Lower jaw 10b is configured to allow loading of sutures (for example, a first suture 80a and a second suture 80b) onto the securing mechanism 17 (loading slot) and then on the needle 55 for advancement through tissue. As shown in FIGS. 1 and 2, suture 80a is loaded through the longitudinal channel and into slot 17 so that a first end of suture 80a is held beneath the lower jaw 10b and the other end of the suture 80a is held above the lower jaw 10b. The ends of suture 80a may be pulled in a proximal direction and to the left side (FIG. 1) for further engagement by needle 55. When needle 55 is actuated and advanced towards the distal end of the lower jaw 10b (by actuating actuator 50, as detailed below), the suture 80a shifts into slot 66 of the needle 55. Once suture 80a has been secured within slot 66 of the needle 55 (and preferably before advancement of the suture 80a by the needle), a second suture 80b may be loaded onto the instrument (as shown in FIG. 3, and as explained in more detail below). The first suture 80a is passed through the tissue to be sutured, by squeezing the handles together and then releasing the pressure on the handles to allow the needle to return to its original position within the longitudinal channel of the lower jaw 10b. The handles are again squeezed together and the second suture 80b is shifted from the securing mechanism (loading slot) 17 and onto the slot 66 of the needle 55 for further engagement and advancing of the suture 80b through tissue.

The suture 80a, 80b is preferably a braided high strength suture such as a Fiberwire™, sold by Arthrex, Inc., Naples, Fla. (for example, a #2 Fiberwire).

The handle assembly includes a first handle, a second handle, a finger lever, a ratchet-like mechanism, and a cam mechanism between the first and second handles. The ratchet-like mechanism is pivotally connected to the handle and the finger lever. The finger lever articulates a jaw (coupled to the tip of the elongated tubular member) relative to the elongated tubular member with the ratcheting mechanism locking and unlocking the jaw in an open or closed position.

Figure 4:
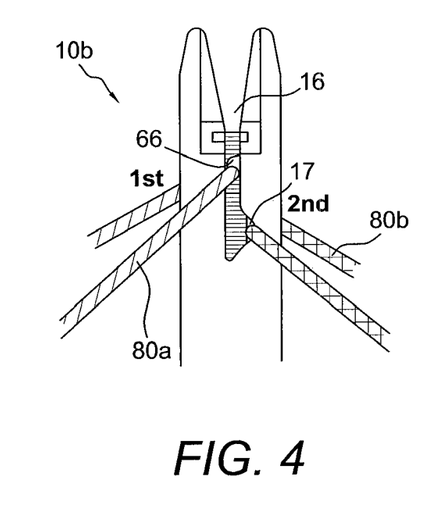
FIG. 4 illustrates a top view of the lower jaw of the suture passing instrument of FIG. 1, with the first flexible strand advanced by the needle and positioned distal to the second flexible strand.
Figure 4A:
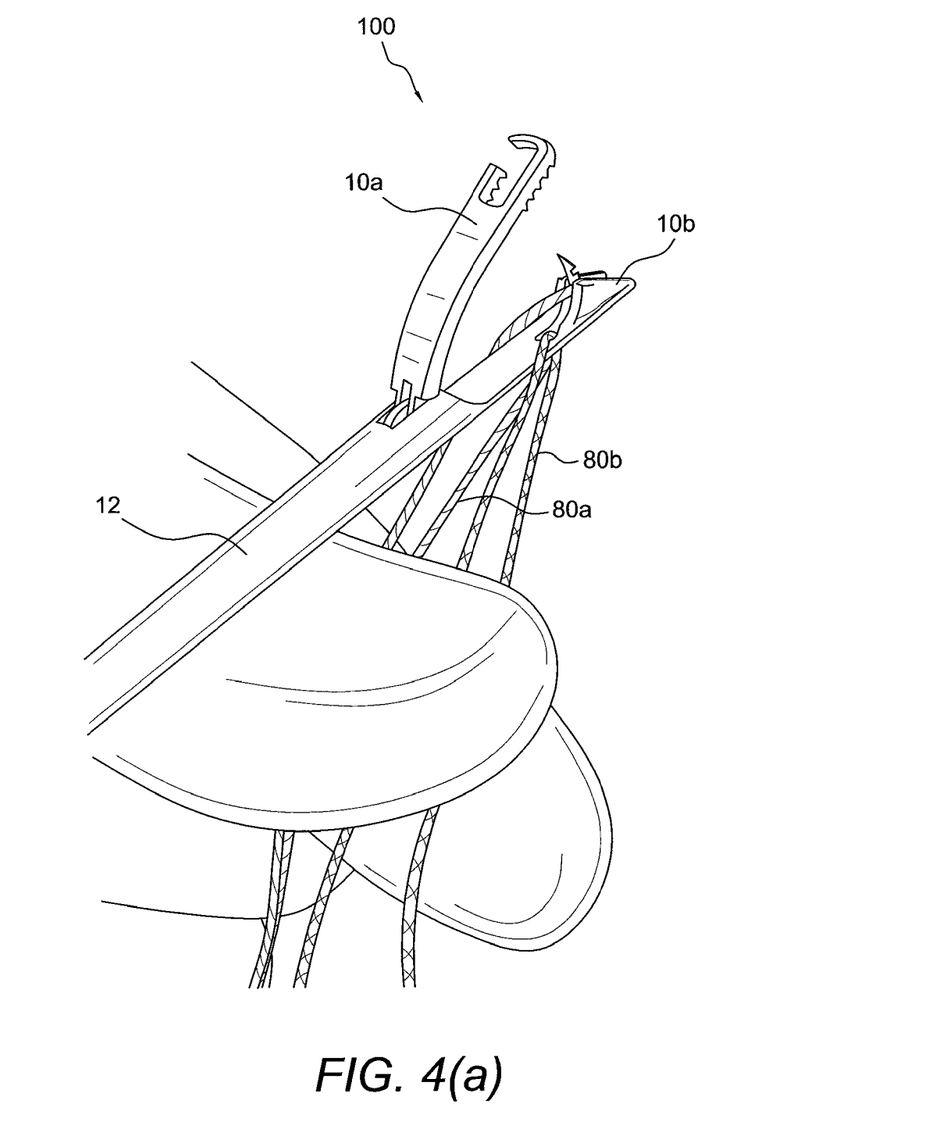
FIG. 4(a) illustrates a view of a distal end of the suture passing instrument of FIG. 1, with the first and second flexible strands pulled back by hand.
Figures 5, 6:
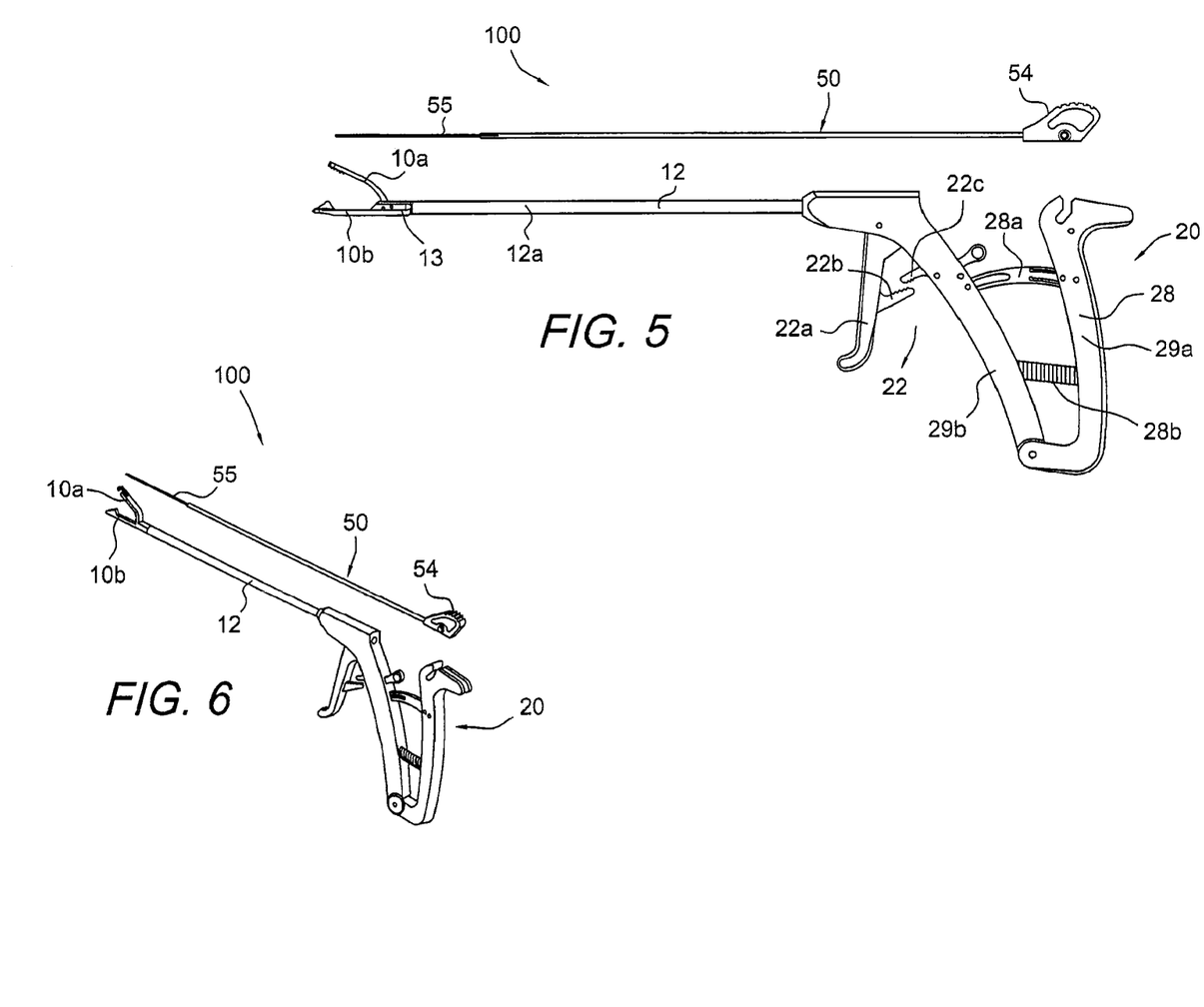
FIGS. 5-7, 7(a), 7(b), 8, 8(a), 8(b), 9, 9(a), 9(b), 10, 10(a), 10(b), 11, 11(a), 12 and 13 illustrate various views of the suture passing instrument of FIG. 1, and at different stages of loading two flexible strands on the lower jaw of the instrument.
Figures 7, 7A, 7B:
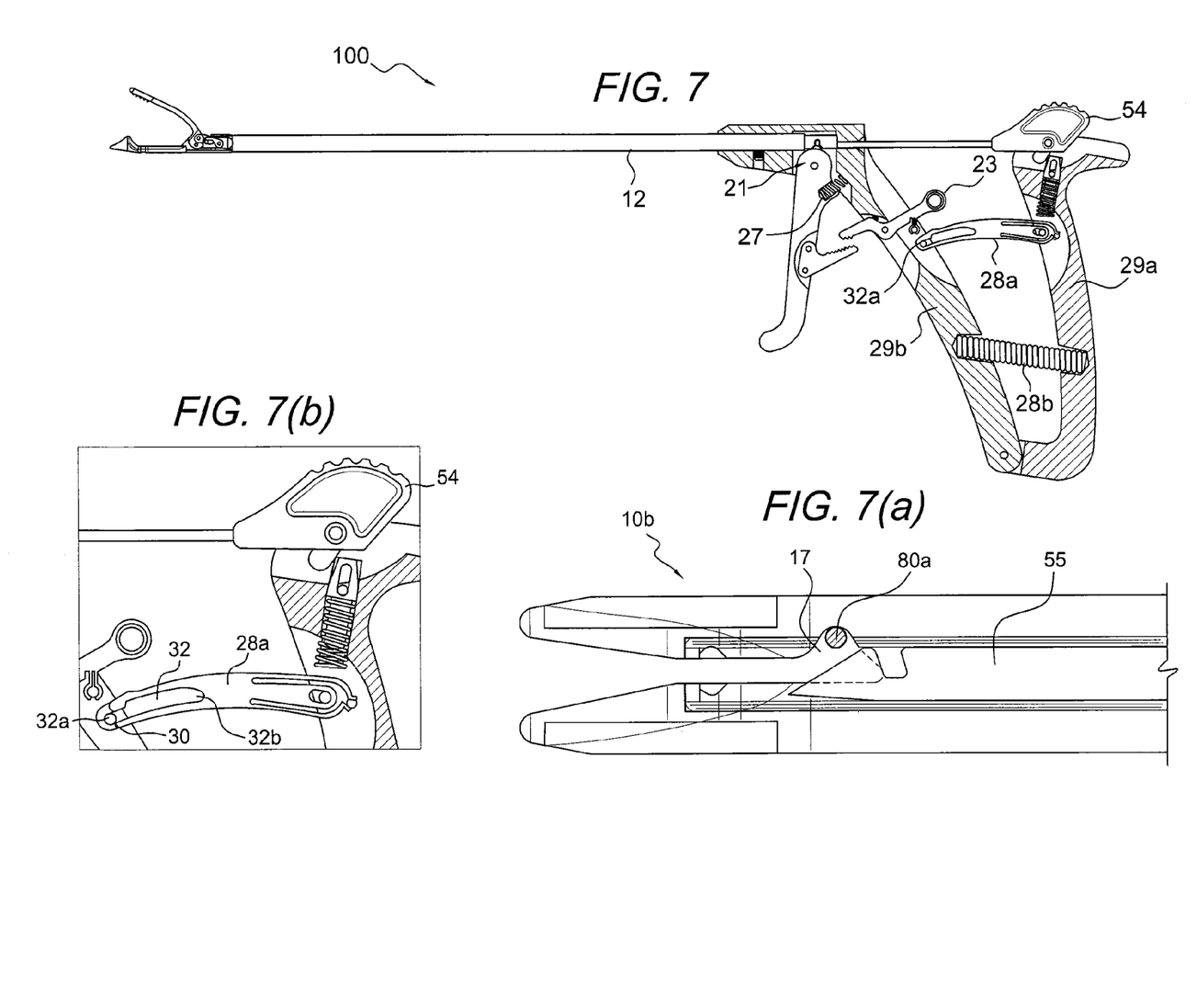

Channel 16 of the lower jaw 10b is configured to allow needle 55 (preferably, a bendable needle 55) to extend through a portion of the channel 16 and exit through opening 15, as illustrated in FIGS. 2 and 4. Needle 55 is substantially disposed within a cannulation 12a passing through the shaft 12. The proximal end of the needle 55 has thumb pad/pusher 54 having a cross pin 51 for engagement with slot 53 provided on the proximal end of the handle. Pushing on the thumb pad 54 moves the cross pin 51 along the slot 53 causing the distal end of the needle 55 to advance into the channel 16 of the lower jaw 10b. When the thumb pad is fully depressed, the slot 66 of the needle 55 is in alignment with the loading slot 17 of the lower jaw 10b. Additionally, the needle 55 may be moved between various positions along the longitudinal channel 16 by moving the proximal and distal ends 29a, 29b of the handle 20 closer to each other.

The lower jaw 10b is configured to house a portion of the needle 55. Needle 55 is substantially disposed within a channel 16 within the lower jaw 10b when the needle is in a non-operative, or non-piercing, position. In an operative position, the needle is advanced distally to exit opening 15 in the lower jaw 10b. The needle 55 is bendable so that it can be moved generally with an axial force and can be bent on a curve, for example, 90 degree to move generally toward the upper jaw 10a. Needle 55 can be bent at any angle and advanced in any direction.

Needle 55 has a pointed tip 60 at a most distal end of the needle and a slot or hook 66 provided in the distal end and preferably on a lateral side of the needle. The pointed tip 60 is designed to pierce the tissue and the slot 66 is designed to capture and carry the suture. Preferably, the needle has a generally flat, narrow and elongate configuration. Needle 55 may preferably be formed of nitinol or other suitable material.

Handle assembly 20 of the suturing instrument 100 illustrated in FIGS. 5-12 is provided at the proximal end 11 of the instrument and includes a ratchet-like mechanism 22 and a handle 28 with ends 29a, 29b, the ratchet-like mechanism 22 being pivotally connected to the handle 28. The ratchet-like mechanism 22 consists of a finger lever 22a with ratchet arms 22b, 22c, and a releaser 23, the ratchet arms 22b, 22c having a plurality of teeth to engage each other. The finger lever 22a and the ratchet arms perform substantially similar to a ratchet and a pawl. The finger lever 22a is pivotally connected by pivot pin 21 to the distal end 29b of the handle. The releaser 23 locks and unlocks the ratchet arms 22b, 22c.

The finger lever 22a is designed to move from a first position to a second position, corresponding to opening and closing the upper jaw 10a. A spring 27 is provided to maintain tension on the finger lever 22a and to force the finger lever 22a to go back to a default position, i.e., the open position. At its default position, the finger lever 22a is farthest from the distal end 29b of the handle 28. The suture passing instrument 100 further includes an actuator which is provided within the shaft 12 and at the distal end of the shaft. A proximal end of the actuator is pivotally connected to the finger lever 22a and a distal end of the actuator is pivotally connected to the upper jaw 10a. The actuator is designed to move the upper jaw 10a from a first position to a second position as the finger lever 22a is moved from a first position to a second position. At the default position of the finger lever 22a, the upper jaw 10a is farthest from the lower jaw 10b. The releaser 23 is designed to move from a first position to a second position, corresponding to locking the ratchet arms together or unlocking the ratchet arms.

The proximal and distal ends 29a, 29b of the handle 28 are connected via a link 28a and tension between the proximal and distal ends may be additionally maintained using spring 28b. The link 28a includes a cam 30 and opening 32. Opening 32 includes a first end 32a and a second end 32b. First end 32a has a smaller width than the second end 32b. When cam 30 is positioned within first end 32a, the cam is in a neutral position, and the handles are a maximum distance apart from each other. As the cam 30 moves along opening 32 towards the second opening, the handles 29a, 29b move towards each other and the cam locks them in a forward position which forces the needle to advance along the longitudinal channel 16. When the handles are squeezed together and the cam is in the second opening, the cam compresses, traveling to the end of the opening 32 and allows the handles to fully release. This moves the needle 55 through the entire longitudinal channel 16 and out the exit opening 15 and returns it back into the shaft 12 of the instrument. As the needle moves through the channel it captures the suture and passes it through the tissue. With handle assembly 20, a surgeon may seize and grasp tissue with jaws 10a, 10b. As detailed below, using pusher 54, the needle is advanced to capture the first suture strand positioned within slot 17, and to further carry and advance the captured first suture strand through the tissue to be sutured. Subsequently, the needle is retracted and advanced to capture the second suture strand and to further advance the captured second suture strand through another region of the tissue.

An exemplary method of employing the suture passing instrument 100 of the present invention begins by loading the needle 55 into the cannulation on the proximal end of the shaft 12 of the suture passing instrument 100, and also two flexible strands 80a, 80b (for example, two flexible suture strands 80a, 80b) onto the bottom jaw of the instrument. The slot on the proximal end of the actuator 50 is engaged securely into a cross pin on the proximal end of handle 28 of the suture passing instrument (FIG. 2(a)).

In an exemplary and illustrative embodiment only, about 1-2 inches of a first flexible strand 80a (for example, a #2 FiberWire) is loaded into the slot on the bottom jaw 10b (FIGS. 1 and 2). Both leads of the first suture 80a (FiberWire) are grabbed and pulled back to the left side. The other hand may be placed on the back end of the instrument 100, with the thumb on top of the thumb pad.

The thumb pad 54 of actuator 50 is pushed down to advance the needle 55 until the first suture 80a shifts into the slot 66 of the needle 55. The needle 55 will retract to its original position as the downward pressure from the thumb is released.

In an exemplary and illustrative embodiment only, about 1-2 inches of a second flexible strand 80b (for example, a #2 FiberWire or a strand different from the first suture strand) is loaded into the slot (FIGS. 3 and 4). The four leads of the first and second strands are grabbed and pulled back with the first loaded suture strands on the left, and the second loaded strands on the right (see FIG. 4(a)). The other hand may be placed on the back end of the instrument, avoiding the front lever.

Figures 8, 8A, 8B:
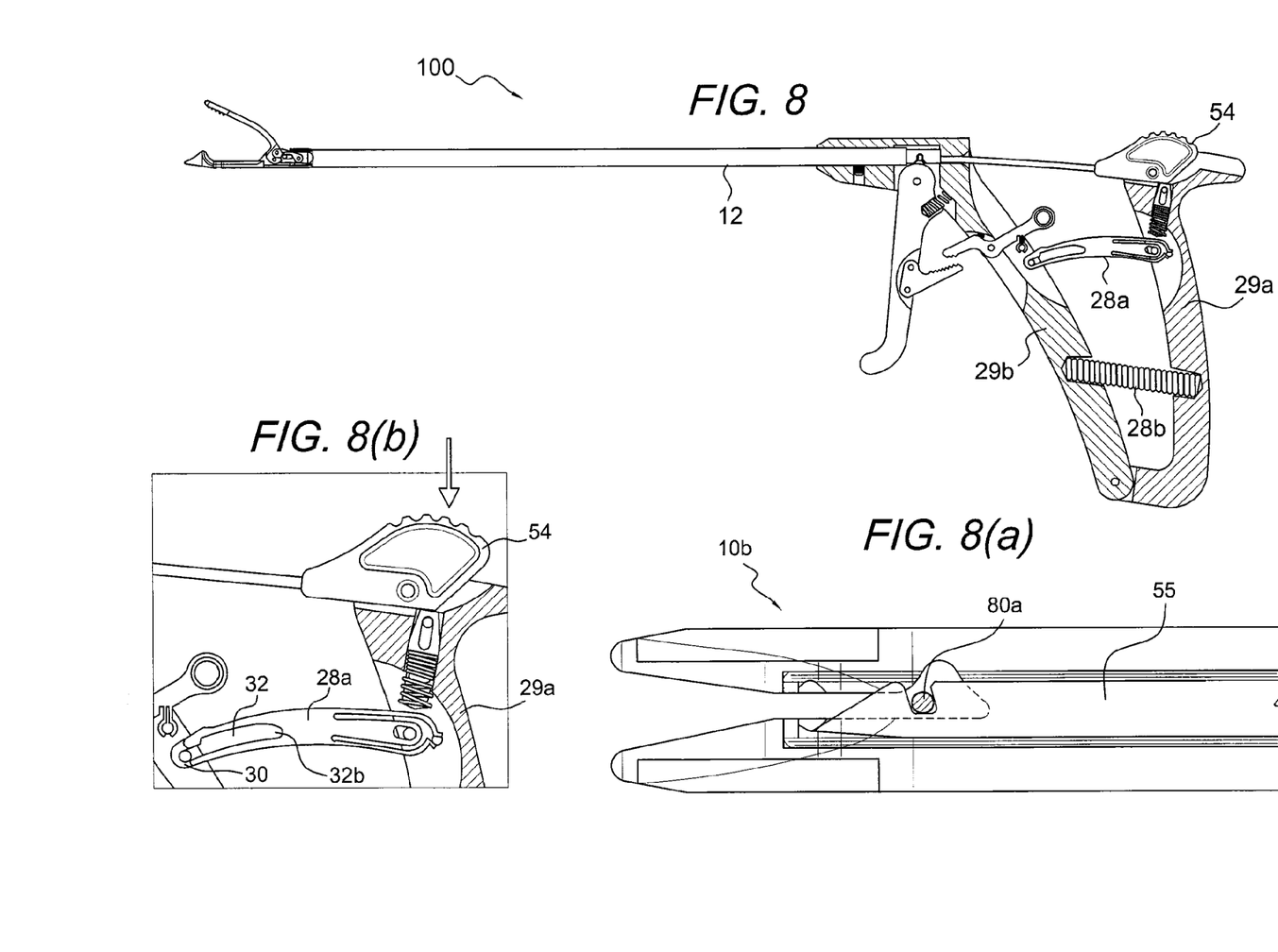

FIGS. 7-11 illustrate additional views of the suture passing instrument 100 showing in more detail the cam function during the loading and delivering of the first and second suture strands 80a, 80b. The loading of the first suture 80a begins by positioning the suture 80a within the slot 17 (FIG. 7a) and pulling the first suture 80a to the left (down in the top view of FIG. 7a). As shown in FIG. 7(a), the needle 55 remains in retracted neutral position and, as shown in FIG. 7(b), the cam 30 also remains in neutral position (with the black button, the thumb pad 54, also remaining in neutral position). The black button (the thumb pad 54) is then pushed down (to advance the needle 55) and released (FIG. 8). As shown in FIG. 8(a), the needle 55 is slightly advanced to capture the first suture strand 80a and, as shown in FIG. 8(b), the cam 30 remains in neutral position (with the black button, the thumb pad 54, also remaining in neutral position).

Figures 9, 9A, 9B:
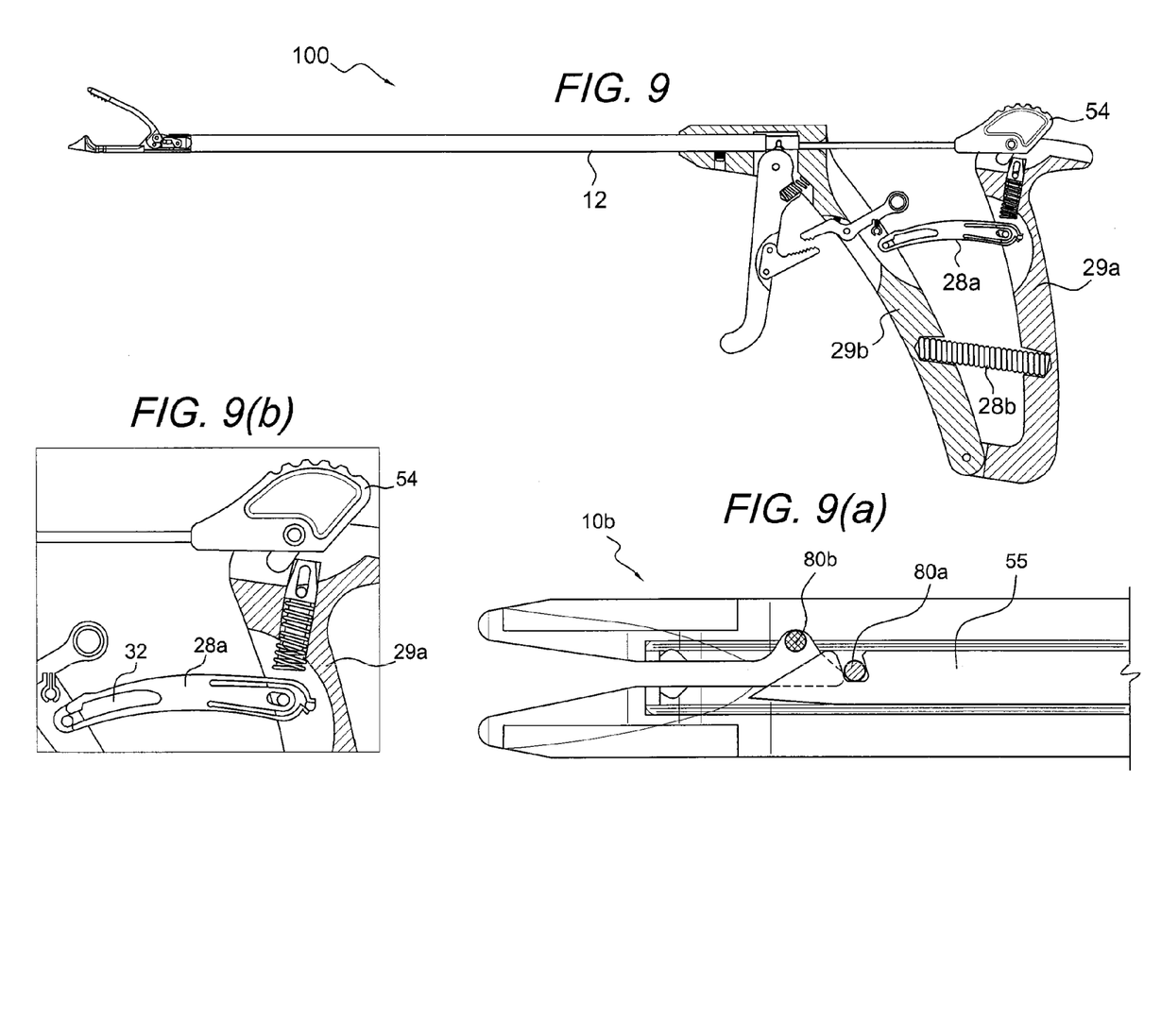

The loading of the second suture 80b begins by positioning the second suture 80b within the slot 17 and pulling the second suture 80b (not shown) to the right (up in the top view of FIG. 9a). As shown in FIG. 9(a), the needle remains in retracted neutral position and, as shown in FIG. 9(b), the cam 30 also remains in neutral position (with the black button also remaining in neutral position).

Figures 10, 10A, 10B:
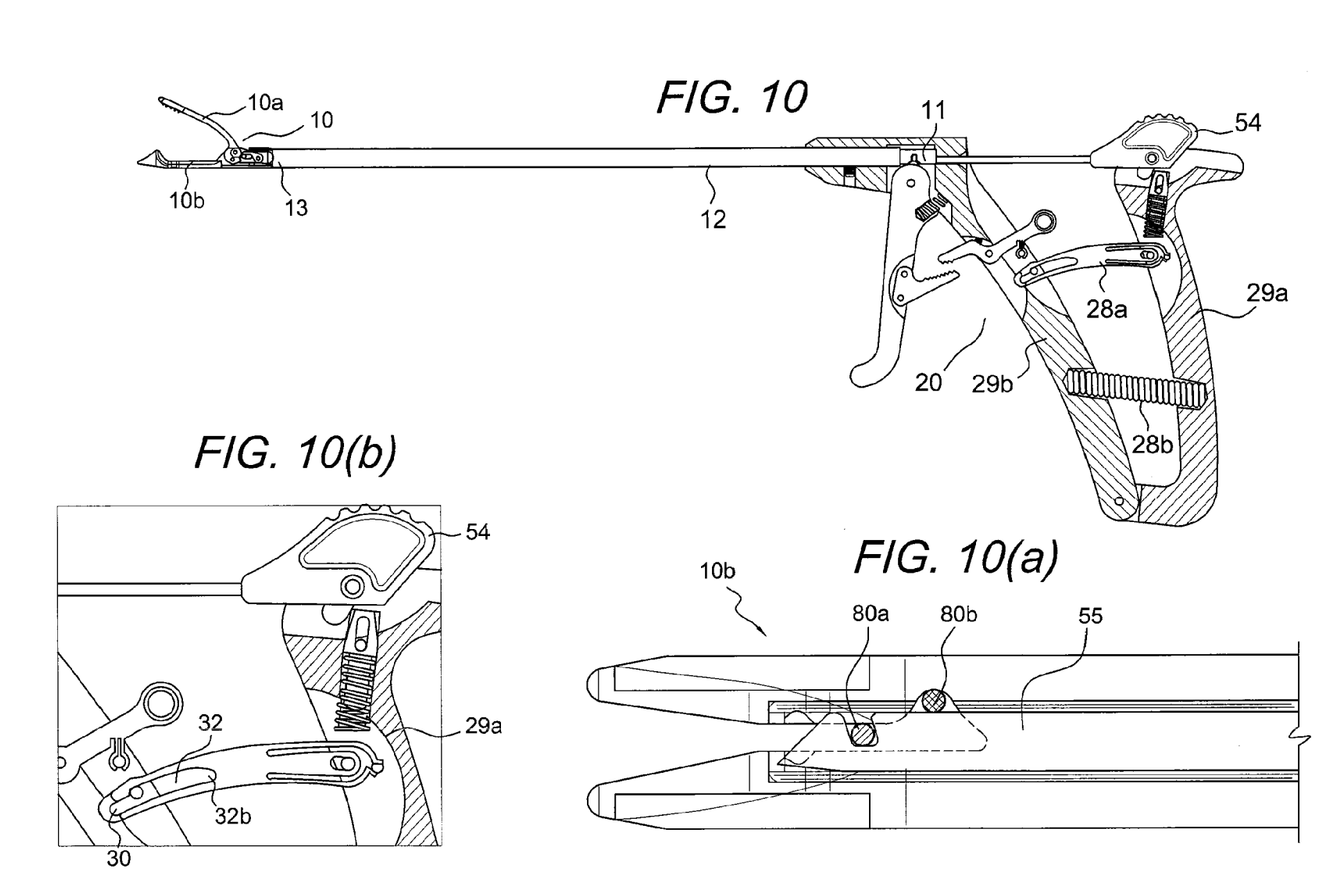

Referring now to FIG. 10, the handle is squeezed to advance the first suture 80a (captured in the needle) ahead of the second suture 80b residing in slot 17. FIG. 10(a) shows the needle 55 being advanced, which positions the first suture 80a ahead of the second suture 80b. As shown in FIG. 10(b), the black button (the thumb pad 54) remains in the neutral position while the cam 30 locks the handle in a forward position.

Figures 11, 11A:
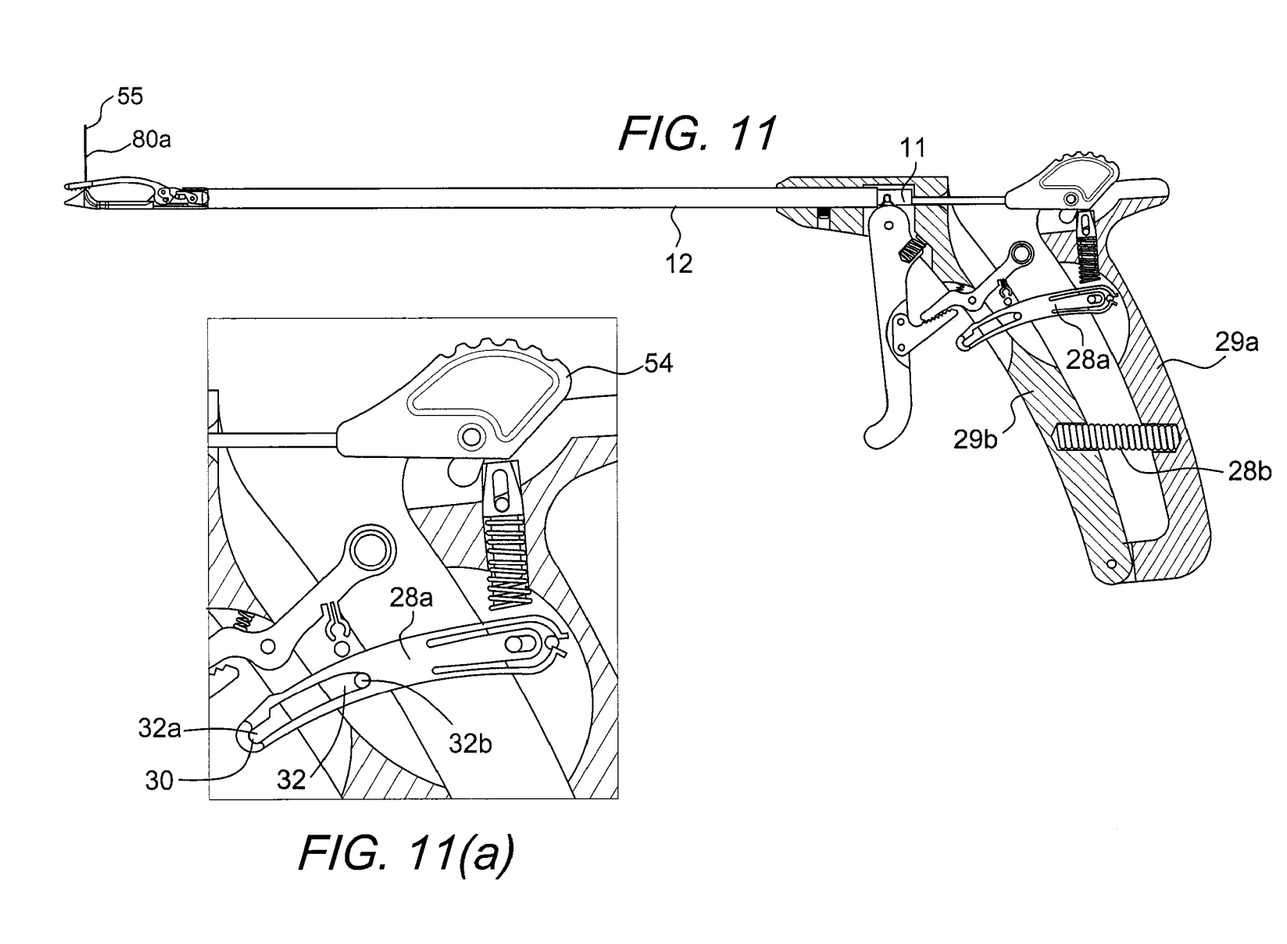
Figures 12, 13:
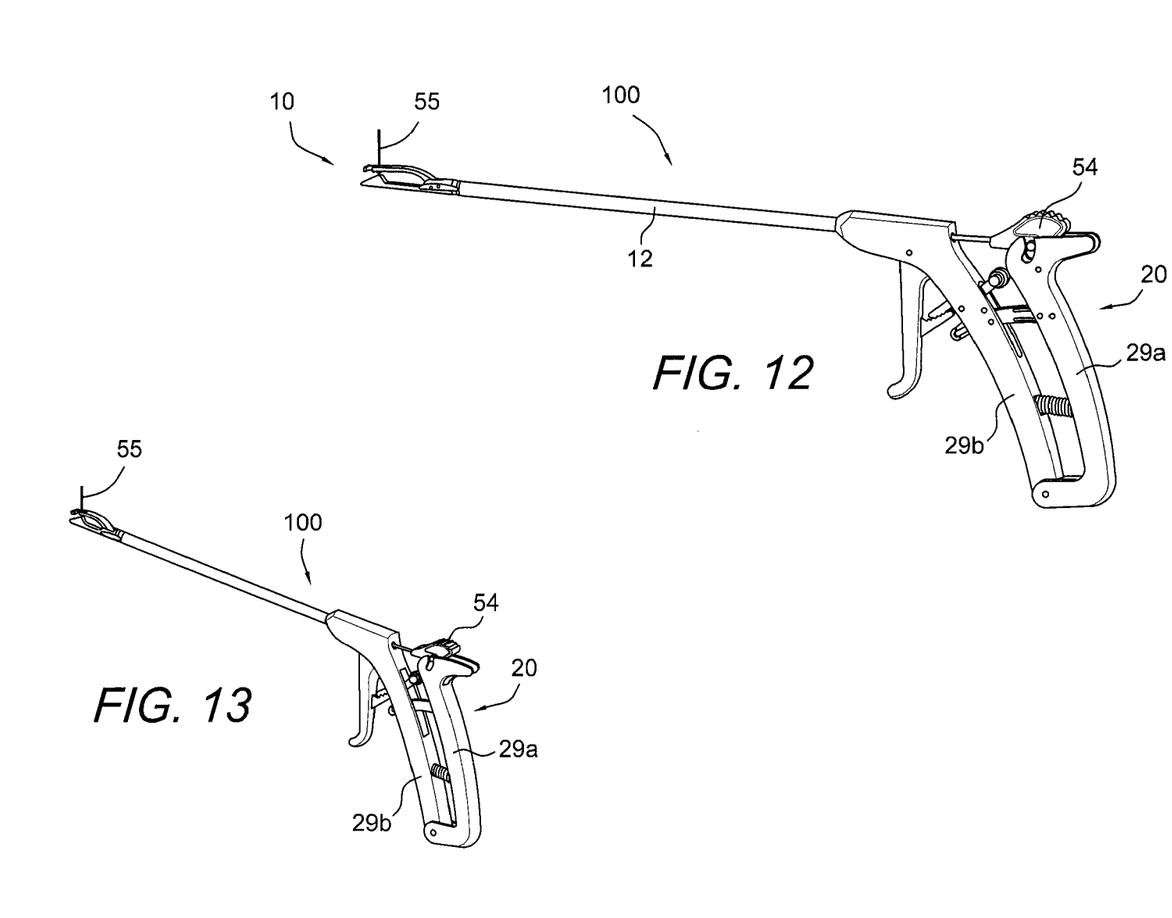
Figures 14A, 14B:
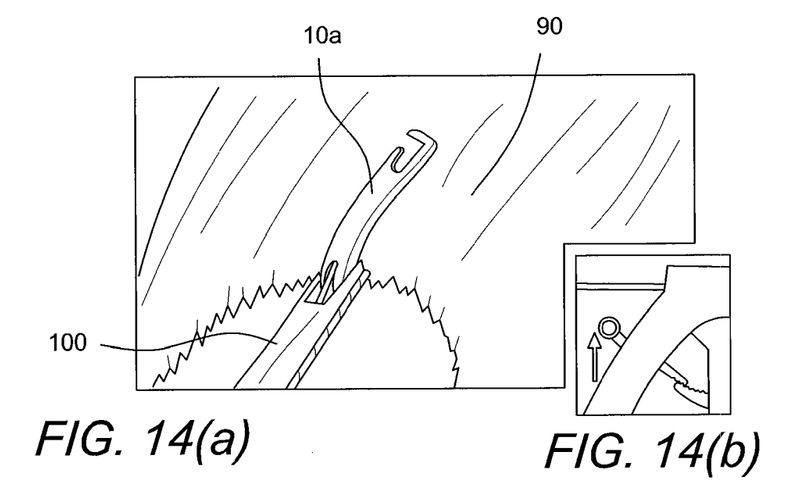
FIGS. 14(a)-(e) and 15 illustrate exemplary suturing steps during an arthroscopic rotator cuff repair and employing the suture passing instrument of the present invention.
Figure 14C:
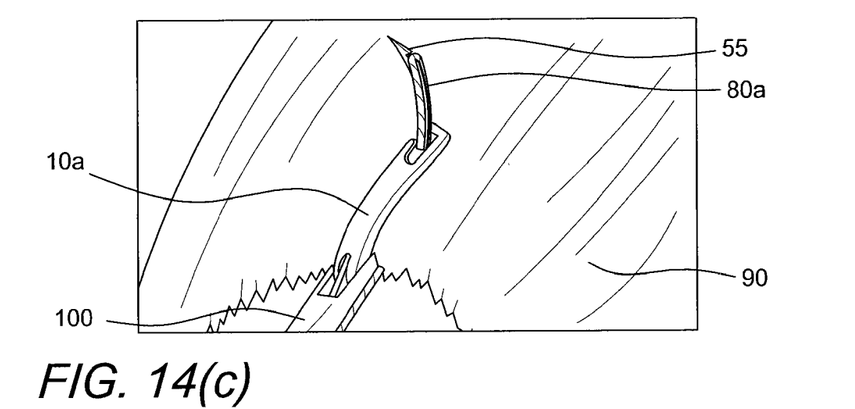
Figure 14D:
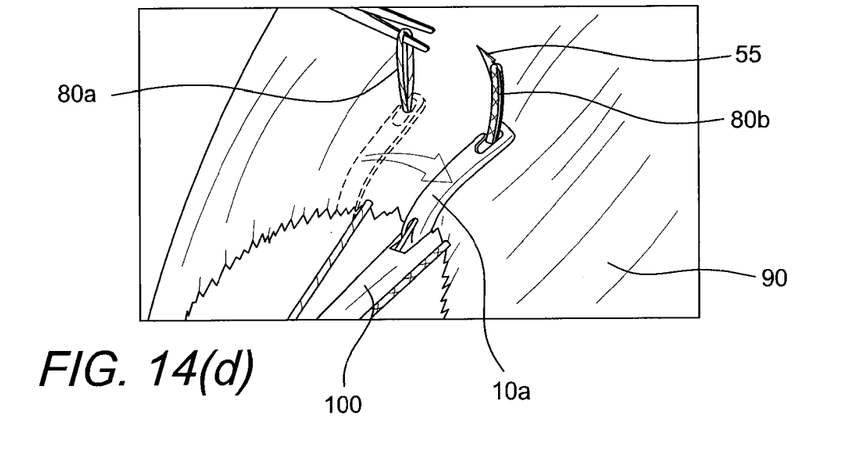
Figure 14E:
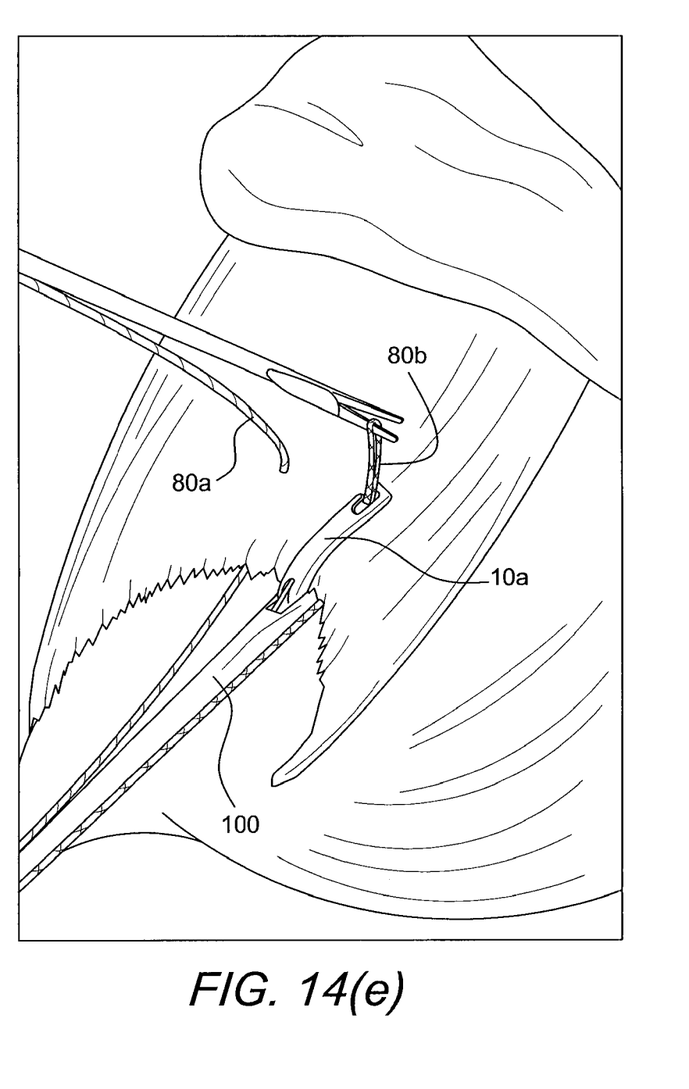

FIG. 11 illustrates the position of the various components of the instrument as during passing of the first suture strand 80a by fully squeezing the handle. The cam will reset and allow the handle to fully open to let the needle retract and grab the second suture 80b. The second suture 80b is then passed by fully squeezing the handle. As shown in FIG. 11(a), the black button remains in the neutral position, while the cam compresses and allows the handle to fully release.

Figure 15:
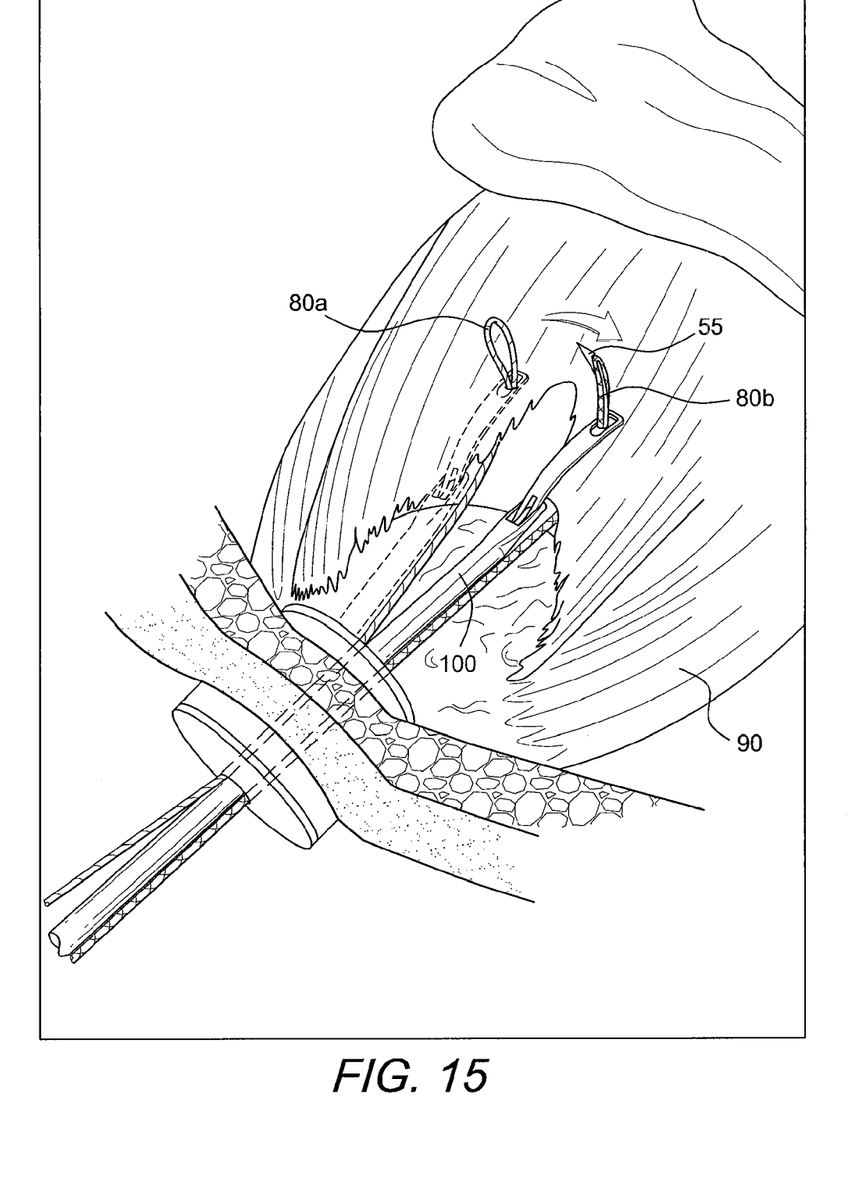

The suture passing instrument 100 of the present invention, described above with reference to FIGS. 1-13, may be employed in various surgical medical procedures for advancing the sutures in the proximity of a surgical site, and for employing the sutures with a cannulated instrument during such surgical procedures, such as arthroscopic rotator cuff repair shown in FIG. 15. Additionally, the suture passing instrument may be utilized in other general surgical and specialty procedures that require suturing at a remote site, such as inside the body. The suture passing instrument of the present invention may be also used in repairs where suture visibility or finger access can be limited.

In an exemplary and illustrative embodiment only, a method of suturing tissue using the suture passing instrument 100 of the present invention comprises the steps of: (i) positioning a first flexible strand within a jaw of suture passing instrument 100; (ii) engaging the first flexible strand with a needle passing through the lower jaw of the instrument; (iii) positioning a second flexible strand within the jaw of the passing instrument; (iv) advancing the needle with the first flexible strand; and (v) passing the first flexible strand through anatomical tissue to be sutured.

According to another exemplary and illustrative embodiment only, a method of suturing a tissue using the suture passing instrument 100 of the present invention comprises the steps of: (i) loading a first suture strand onto a bottom jaw of a suture passing instrument; (ii) capturing the first suture strand with a needle; (iii) loading a second suture strand onto the bottom jaw of the suture passing instrument; (iv) closing the jaws on a desired, first region of the tissue using a finger lever and advancing the needle (with the first suture strand engaged and captured thereon) through a first region of the tissue; (v) retracting the needle; (vi) capturing the second suture strand with the needle and advancing the needle (with the second suture strand engaged and captured thereon)

through a second region of the tissue; and (vii) retrieving the first and second sutures using a retriever or grasper.

Reference is now made to FIGS. 14(a)-(e) and 15 which illustrate exemplary suturing steps during an arthroscopic rotator cuff repair and employing the suture passing instrument 100 of the present invention. Once suture passing instrument 100 has been loaded with needle 55 and flexible suture strands 80a, 80b, the upper jaw 10a and the lower jaw 10b are brought together (in a closed position) and the suture passing instrument 100 is advanced into the proximity of tissue 90 to be sutured. The two jaws may be held together (in the closed position) by actuating the releaser 22c (from an "Unlock" position to a "Lock" position). The upper jaw 10a is then disengaged from the lower jaw 10b by releasing the finger lever 22a and a desired bite of tissue is grasped (see FIGS. 14(a) and 14(b)).

With the jaws closed around the tissue (and preferably with the releaser 22c in the "Lock" position), the proximal and distal members 29a, 29b of the handle 28 of the handle assembly 20 are squeezed together so that the needle is advanced distally, exiting the opening 15 on the lower jaw 10b. Once the loaded instrument 100 is gently squeezed with the palm of the hand, the needle 55 advances and will pass the first loaded suture 80a first (see FIG. 14(c)). The needle is then retracted, and will engage and pass the second loaded suture 80b. The passed sutures are then retrieved (see FIGS. 14(d) and 14(e)).

While the suture passing instrument 100 may be particularly useful for performing remote procedures through access sheaths, trocars and cannulated surgical instruments, it will also find use in open surgical procedures. In addition, although the suture passing instrument 100 of the present invention has been described above as being configured for loading two flexible strands, the suture passing instrument 100 may be also employed with only one loaded flexible strand or with any plurality of flexible strands.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A suture passing instrument comprising:
   an elongate body having a distal end, a proximal end, and a cannulation;
   a first jaw member integral to the distal end of the elongate body, the first jaw member having a securing mechanism and a passage;
   a single needle wherein the single needle passes through the cannulation of the elongate body and through the passage of the first jaw member;
   a second jaw member mounted to the distal end of the elongate body and pivotally connected to the first jaw member such that the second jaw member is moveable with respect to the first jaw member;
   a first flexible strand and a second flexible strand loaded onto the first jaw member, the first flexible strand secured within a slot of the single needle, and the second flexible strand being secured onto the securing mechanism of the first jaw member; and
   a handle assembly configured to move the single needle from a first position to a second position and to sequentially engage each of the first flexible strand and the second flexible strand with the single needle and pass each of the first flexible strand and second flexible strand independently of each other, wherein when the first flexible strand and second flexible strand are loaded onto the first jaw member, the first flexible strand is offset from the second flexible strand with respect to a most distal tip of the first jaw, and the first flexible strand is positioned distally to the second flexible strand relative to the handle assembly.

2. The suture passing instrument of claim 1, wherein the securing mechanism is a slot, a wedge, or a groove.

3. The suture passing instrument of claim 2, wherein the securing mechanism is a V-shaped groove.

4. The suture passing instrument of claim 1, wherein the slot is configured to securely engage each of the first flexible strand and second flexible strands.

5. The suture passing instrument of claim 1, wherein the first jaw member further comprises an opening at a distal end of the first jaw to allow the needle to pass therethrough.

6. The suture passing instrument of claim 1, wherein the elongate body is a shaft.

7. The suture passing instrument of claim 1, wherein the second jaw member is curve-shaped in a humpback configuration with a given radius of curvature.

8. The suture passing instrument of claim 1, wherein the handle assembly further comprises a handle with a proximal end and a distal end, a ratchet mechanism comprising a finger lever with a ratchet and a releaser with a hook, the finger lever and the releaser being pivotally connected to the distal end of the handle, and a cam mechanism.

9. The suture passing instrument of claim 8, wherein the cam mechanism is connected to the proximal end and the distal end of the handle, and wherein the cam mechanism includes an opening with a first end and a second end, so that when the first end of the opening is in contact with the distal end of the handle, the distal end and the proximal end of the handle are at a maximum distance apart from each other, and when the second end of the opening is in contact with the distal end of the handle, the distal end and the proximal end of the handle are pushed toward each other.

10. The suture passing instrument of claim 8, wherein the proximal and distal ends of the handle are linkably connected and tension between the proximal and distal ends of the handle is maintained using springs.

* * * * *